United States Patent [19]

Schoon

[11] Patent Number: 5,523,076
[45] Date of Patent: Jun. 4, 1996

[54] ARTIFICIAL NAIL COMPOSITION

[75] Inventor: Douglas D. Schoon, Newport Beach, Calif.

[73] Assignee: Creative Nail Design, Inc., Vista, Calif.

[21] Appl. No.: 299,476

[22] Filed: Aug. 31, 1994

Related U.S. Application Data

[63] Continuation of Ser. No. 97,872, Jul. 27, 1993, abandoned.

[51] Int. Cl.$^6$ .............................. A61K 7/04; A61K 7/043
[52] U.S. Cl. ........................................................... 424/61
[58] Field of Search ................................................. 424/61

[56] References Cited

U.S. PATENT DOCUMENTS

| | | | |
|---|---|---|---|
| 3,749,769 | 7/1973 | Sugiyama et al. | 424/61 |
| 3,773,710 | 11/1973 | Victorius | 260/41 |
| 3,780,003 | 12/1973 | Seymour | 260/86.1 |
| 3,846,368 | 11/1974 | Pettit | 260/39 |
| 3,926,892 | 12/1975 | Holcombe, Jr. | 260/29.6 |
| 3,967,045 | 6/1976 | Kurobe et al. | 428/463 |
| 4,229,431 | 10/1980 | Lee, Jr. et al. | 424/61 |
| 4,396,476 | 8/1983 | Roemer et al. | 204/159.16 |
| 4,649,045 | 3/1987 | Gaske et al. | 424/61 |
| 5,098,952 | 3/1992 | Blasko et al. | 525/123 |

FOREIGN PATENT DOCUMENTS

| | | | |
|---|---|---|---|
| 1952721 | 10/1970 | Germany | 424/61 |
| 0085370 | 10/1983 | Germany | 424/61 |

*Primary Examiner*—Peter F. Kulkosky
*Attorney, Agent, or Firm*—Brown, Martin, Haller & McClain

[57] ABSTRACT

An artificial human nail structure is described which is formed of polymerized alkyl methacrylate and hydroxyalkyl methacrylate in a weight ratio in the range of 1–50 parts of alkyl methacrylate per part of hydroxyethyl methacrylate, preferably a ratio of 2–20:1, and more preferably of 3–10:1, and wherein said alkyl moiety of either is any $C_1$–$C_4$ alkyl, preferably ethyl. The artificial nail coating can be easily applied, polymerizes readily and rapidly without catastrophic crystallization and produces a transparent and easily shaped artificial nail structure. Also disclosed is an artificial human nail surface precursor having as its principal component a mixture of alkyl methacrylate and hydroxyalkyl methacrylate in the above mentioned weight ratio. Nail materials formed exhibit high impact resistance, improved stiffness, good flexural strength, resistance to cracking and breaking, good workability, improved compatibility with the natural nail surface, good transparency, clarity and moldability, may need not primer, has increased adhesion, better stability, and have no tendency toward catastrophic crystallization.

8 Claims, No Drawings

ARTIFICIAL NAIL COMPOSITION

This is a continuation of application Ser. No. 08/097,872, filed Jul. 27, 1993, now abandoned.

BACKGROUND OF THE INVENTION

1. Field of the Invention

The invention herein relates to composition and structures for artificial human nails. More particularly, it relates to such compositions formed of polymeric materials.

2. Description of the Prior Art

Artificial finger nails (and toe nails) are major items of personal fashion. Artificial nails are normally formed by coating (as by applying with a brush) a viscous liquid layer of polymerizable material on the surface of the natural nail, shaping (as with a brush) and then allowing the coating material to polymerize and harden. In many cases polymerization can be speeded up by use of a catalyst or accelerator incorporated into the coating. Once polymerized and hardened, the artificial nail can be shaped and polished to present an attractive and natural appearance.

There are several basic types of artificial nail materials. One type exhibits a significant amount of vapor evolution during curing. The vapors frequently have a noticeable odor. While that odor quickly dissipates for the wearer, it persists in nail shops and the technicians who apply the nail surfaces to the customers are subjected to extended exposure to the vapors. In addition, this type of product shows limited strength and can have a pronounced tendency to discolor, crystallize and lift from the nail plate. The common monomeric compounds which are frequently used as polymerizable components of this type of nail surface are ethyl methacrylate (EMA) and isobutyl methacrylate.

A different type of nail materials are called "odorless materials," since they produce little or no vapor during polymerization. This type of material, however, has had its own disadvantages. They often form "skins" (i.e., unpolymerized surface layers) which must be removed. They form relatively thick coatings and cannot be readily picked up and coated by the nail technician's brush. In addition, they have a definite tendency to yellow and become brittle with age. Their use also requires a significant change in the conventional application techniques used by nail technicians, a change which many technicians dislike and resist. A common component used in this type of materials is hydroxyethyl methacrylate (HEMA).

Speed of polymerization (hardening or curing) is an important factor in the success of artificial nail products. Acceleration of reaction can usually be obtained only by using excess catalyst or accelerator or by heating. Heating, however, is impractical for artificial nail surfaces simply because the technician cannot apply significant heat to a customer's hands. Use of excess catalyst or accelerator is also undesirable because it usually makes the nail composition unacceptably brittle, such that the finished nail will break easily, and discolored. In the past, the prior art has attempted to overcome the problem of brittleness by adding rubber compounds to strengthen the nail, but the resulting phase separation caused by the rubber makes the composition opaque or translucent rather than having the desired transparency.

Another very significant problem in the application of artificial nail compositions, particularly in the nail systems utilizing EMA, has been "catastrophic crystallization." This occurs when the artificial nail composition, prior to becoming fully polymerized and hardened, comes in contact with cool air or air drafts. This results in the formation of crystal-like regions throughout the entire depth of the coating. Polymerization of the coating thereafter does not occur in these regions so that the overall artificial nail structure does not form properly. In such cases, the nail technician must remove the entire coating and start over with a completely new coating application. The additional length of time needed to completely redo a catastrophically crystallized nail coating is objected to by both the technicians and the customers as a time-consuming task for the technician and a major inconvenience for the customer.

SUMMARY OF THE INVENTION

The invention herein therefore advantageously involves a novel coating composition which can be easily applied, polymerizes readily and rapidly without catastrophic crystallization, may not require a primer, does not discolor, and produces a transparent and easily shaped artificial nail structure. In a broad form, therefore, the invention herein is an artificial human nail structure consisting essentially of polymerized alkyl methacrylate (AMA) and hydroxyalkyl methacrylate (HAMA), where the alkyl moiety of either is a $C_1$–$C_4$ alkyl, in a weight ratio in the range of 1–50 parts of alkyl methacrylate per part of hydroxyalkyl methacrylate. In preferred embodiments the ratio of parts of alkyl methacrylate per part of hydroxyalkyl methacrylate is in the range of 2–20:1, and more preferably in the range of 3–10:1. The alkyl moiety in either is preferably ethyl, although the alkyl moiety in one methacrylate need not be the same as in the other.

In another embodiment, the invention is an artificial human nail surface precursor consisting essentially of a mixture of alkyl methacrylate and hydroxyalkyl methacrylate, where the alkyl moiety of either is a $C_1$–$C_4$ alkyl, in a weight ratio in the range of 1–50 parts of alkyl methacrylate per part of hydroxyalkyl methacrylate. In preferred embodiments the ratio is in the range of 2–20:1, and more preferably in the range of 3–10:1. The alkyl moiety in either is preferably ethyl, although the alkyl moiety in one methacrylate need not be the same as in the other.

Nail materials of the present invention have been found to exhibit high impact resistance, improved stiffness, resistance to cracking and breaking, good workability, improved compatibility with the natural nail surface, as well as good flexural strength, transparency, clarity and moldability. They also provide improved adhesion to the nail plate, reduced odor and increased strength. Most importantly, however, the present compositions exhibit no tendency to catastrophic crystallization.

DETAILED DESCRIPTION AND PREFERRED EMBODIMENTS

The invention herein is a precisely defined artificial nail coating precursor composition and the resulting artificial nail structure formed by polymerization of that precursor. While the two principal components of the precursor and nail surface have been known separately as components in artificial nail compositions in the past, they have never before been used together as the principal components of a composition in the manner described herein and the unique and beneficial properties of such a new composition have heretofore been unknown and unrecognized.

Specifically, the principal components of the composition are alkyl methacrylate and hydroxyalkyl methacrylate, where the alkyl moiety of either is any $C_1$–$C_4$ alkyl, in a ratio of 1–50 parts of alkyl methacrylate and hydroxyalkyl methacrylate (all parts and percentages mentioned herein are by weight unless otherwise specified). Preferably the ratio will be in the range of 2–20:1 and more preferably 3–10:1. The alkyl moiety in either is preferably ethyl, although the alkyl moiety in the alkyl methacrylate need not be the same alkyl as in the hydroxyalkyl methacrylate. Ethyl methacrylate (EMA) and hydroxyethyl methacrylate (HEMA) are the preferred materials, and for brevity herein the invention will be exemplified below by the EMA/HEMA embodiment, except where other embodiments are specified. It will be understood, of course, that the methyl, normal propyl, isopropyl, normal butyl, isobutyl and tertiary butyl alkyl methacrylates and hydroxyalkyl methacrylates are also within the scope of the invention.

In their initial form, the monomeric EMA and HEMA will be liquids which are blended in the desired ratio. (Those skilled in the art will recognize that commercial monomers may have small amounts—usually less than 1%—of other branched or unbranched-materials present. These do not significantly affect the current invention.) A polymerization (cross-linking) catalyst for methacrylate monomers, such as benzoyl peroxide, polymeric EMA, polymeric HEMA, copolymeric EMA/HEMA, polymeric methyl methacrylate (MMA) or copolymeric MMA/EMA, will also be present in the mixture. The concentration of the catalyst (which is usually in powdered form) will be in the range of 0.25 to 1.0 parts of powdered catalyst per part of the combined liquid EMA and HEMA monomers. An accelerator for the reaction may also be present. Such catalysts and accelerators are conventional and well known in the art.

There may be additional conventional materials present which do not adversely affect the properties of the composition. These may include colorants, plasticizers, toughening agents, cross-linkers and ultraviolet light absorbers (the last component being used to slow any tendency of the polymerized nail composition to yellow from ambient UV radiation).

Compositions of the present invention have been found to exhibit higher impact resistance than any of the materials of the prior art, including those using EMA or HEMA alone or in combination with components with other than each other. Similarly, the new compositions exhibit improved stiffness, resistance to cracking and breaking and workability. They particularly have improved compatibility with the natural nail surface, to the point where in most cases it is not necessary to use a methacrylate acid primer on the natural surface before application of the present composition. The ability to dispense with primer is a major advantage for both technicians and customers. The lack of need to use a primer reduces the application time, increases safety, improves natural nail health, allows the customer to spend less time having her nails done and increases the number of customers that a nail technician can see in a work day. Further, the transparency, clarity and moldability of the new compositions surpass the comparable properties of the best quality prior art nail compositions. (Moldability relates to the ease with which the technician can shape the polymerized artificial nail structure, and is referred to as "machinability" by nail technicians.)

Most importantly, however, the present compositions exhibit no tendency to catastrophic crystallization. Extended testing has indicated that no instance of catastrophic crystallization occurred in any of the test samples. At worst minor surface crystallization in the form of a light dust occurred on the outer surface of the nail coating but did not penetrate into the body of the coating. The minor surface crystallization was easily brushed away and did not affect the polymerization of the overall coating. In particular, there was no need to have the entire artificial nail surface stripped away and an entirely new coating applied, as had been required in the past.

The improved strengths obtained by the compositions of this invention are clearly illustrated by the following data. In the tests represented, EMA/HEMA monomer blends with different ratios of EMA:HEMA were polymerized with a benzoyl peroxide/EMA/methyl methacrylate powdered polymer blend as a catalyst, and cured for one week at 23° C. Flexural strength was then measured and is reported below; the control was a 100% EMA product.

TABLE

| HEMA Content, % | Maximum Flexural Strength, Pa |
|---|---|
| 0 (100% EMA) | 216 |
| 5 | 237 |
| 10 | 245 |
| 12 | 263 |
| 15 | 265 |
| 18 | 267 |
| 20 | 258 |
| 25 | 260 |
| 30 | 263 |

It will be evident that the incorporation of HEMA, even in relatively low concentrations, substantially improved the strength of the product. Above about 10–11% HEMA the strength property reaches a plateau level, where addition of more HEMA maintains substantially equivalent strength. Thus the optimum upper limit will usually be determined by factors other than strength, such as relative cost of EMA and HEMA, blending considerations, polymerization time, and so forth. The principal factor determining the optimum upper limit will often be the increasing degree of brittleness which results as higher HEMA contents are used, although brittleness will also be affected by the amount of plasticizer which may be present.

The exact mechanism responsible for the unexpectedly superior properties of the present composition is not known with certainty. It is believed, however, that the improved compatibility with the natural nail surface and the improved strength occur because there is formation of hydrogen bonds between the hydroxy moiety of the coating and the natural nail surface, rather than any kind of ionic bonding, and intermolecular hydrogen bonds formed within the coating itself. Similarly, it is believed that the two components, when used in the precise and narrowly defined ratios set forth herein, interact synergistically during polymerization in a manner which results in enhancement of the beneficial properties of the materials and suppression of their less desired or detrimental properties.

It will be evident from the above that there are other embodiments of the composition, which while not expressly described above, are clearly within the scope and spirit of the invention. The description above is therefore intended to be exemplary only and the scope of this invention is to be limited solely by the appended claims.

I claim:

1. An artificial human nail structure attached to a human nail and extending beyond the tip of the nail, consisting essentially of polymerized alkyl methacrylate and hydroxyalkyl methacrylate in a predetermined weight ratio for resisting catastrophic crystallization, the weight ratio being in the range of 2–20:1 alkyl methacrylate: hydroxyalkyl methacrylate, wherein said alkyl moiety of either is a $C_1$–$C_4$ alkyl, wherein said alkyl methacrylate and hydroxyalkyl methacrylate are substantially completely polymerized in the presence of crosslinker and polymerization catalyst on the nail to form a three-dimensional cross-linked polymer structure.

2. An artificial human nail surface as in claim 1 wherein said ratio is in the range of 3–10:1.

3. An artificial human nail surface as in claim 1 wherein said alkyl moiety is ethyl in both said alkyl methacrylate and hydroxyalkyl methacrylate.

4. An artificial human nail surface as in claim 1 wherein said alkyl moiety is one $C_1$–$C_4$ alkyl in said alkyl methacrylate and a different $C_1$–$C_4$ alkyl in said hydroxyalkyl methacrylate.

5. An artificial human nail surface as in claim 4 wherein said alkyl moiety is ethyl in either of said alkyl methacrylate and hydroxyalkyl methacrylate or a different $C_1$–$C_4$ alkyl in the other.

6. A method of forming an artificial human nail surface extending beyond the tip of an underlying human nail, comprising the steps of:

taking a first component consisting essentially of a mixture of alkyl methacrylate and hydroxyalkyl methacrylate in an unpolymerized state and in a predetermined weight ratio for resisting catastrophic crystallization, and a cross-linker, the ratio being in the range of 2–20:1 alkyl methacrylate: hydroxyalkyl methacrylate, wherein the alkyl moiety of either is a $C_1$–$C_4$ alkyl, and a separate, second component consisting essentially of a polymerization initiator catalyst for said first component;

mixing together said first and second component only immediately prior to or on application to a human nail surface so that no polymerization occurs prior to application of the mixture to the human nail surface;

applying said mixture as a coating to a surface of a natural human nail and allowing said catalyst and cross-linker to catalytically polymerize said mixture only after application to said nail surface until said first component is substantially completely polymerized by cross-linking between the molecular constituents of said two monomers into a three-dimensional, cross-linked polymer structure; and allowing said coating to harden to form an artificial human nail surface which extends beyond the tip of the underlying nail, whereby the coating has improved resistance to catastrophic crystallization during polymerization.

7. The method as claimed in claim 6, wherein the weight ratio is in the range of 3–10:1.

8. A method of forming an artificial human nail surface, comprising the steps of:

taking a first component consisting essentially of a mixture of ethyl methacrylate and hydroxyethyl methacrylate in an unpolymerized state and in a predetermined weight ratio for resisting catastrophic crystallization, and a cross-linker, the ratio being in the range of 3–10:1 ethyl methacrylate: hydroxyethyl methacrylate, and a separate, second component consisting essentially of a polymerization initiator catalyst for said first component;

mixing together said first and second component only immediately prior to or on application to a human nail surface so that no polymerization occurs prior to application of the mixture to the human nail surface;

applying said mixture as a coating to a surface of a natural human nail and allowing said catalyst and cross-linker to catalytically polymerize said mixture only after application to said nail surface until said first component is substantially completely polymerized by cross-linking between the molecular constituents of said two monomers into a three-dimensional, cross-linked polymer structure; and allowing said coating to harden to form an artificial human nail surface which extends beyond the tip of the underlying nail, whereby the coating has improved resistance to catastrophic crystallization during polymerization.

* * * * *